(12) United States Patent
Hogan et al.

(10) Patent No.: US 6,664,059 B2
(45) Date of Patent: Dec. 16, 2003

(54) ASSAY FOR PROPENSITY FOR CANINE MALIGNANT HYPERTHERMIA

(75) Inventors: Kirk J. Hogan, Madison, WI (US); David B. Brunson, Madison, WI (US); Monica C. Roberts, St. Paul, MN (US); James R. Mickelson, St. Paul, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/908,410

(22) Filed: Jul. 18, 2001

(65) Prior Publication Data

US 2003/0104382 A1 Jun. 5, 2003

(51) Int. Cl.[7] .................................................. C12Q 1/68
(52) U.S. Cl. ........................ 435/6; 435/91.2; 435/91.1; 536/23.1; 536/24.3; 536/24.31; 536/21.33
(58) Field of Search .................... 435/6, 91.1, 91.2; 536/23.1, 24.3, 24.31, 24.33

(56) References Cited

U.S. PATENT DOCUMENTS

| | | |
|---|---|---|
| 5,702,919 A | 12/1997 | Nash et al. |
| 5,804,388 A | 9/1998 | Aguirre et al. |
| 6,001,976 A | 12/1999 | MacLennan et al. |
| 6,063,600 A | 5/2000 | Fuller et al. |
| 6,074,832 A | 6/2000 | Venta et al. |
| 6,140,115 A | 10/2000 | Kolodny et al. |
| 6,201,114 B1 | 3/2001 | Aguirre et al. |
| 6,210,897 B1 | 4/2001 | Anderrson et al. |
| 6,251,632 B1 | 6/2001 | Lillicrap et al. |

OTHER PUBLICATIONS

Roberts et al. Genbank Accession No. AF3021228, Oct. 2, 2001.*
Priat et al. "A whole–genome radiation hybrid map of the dog genome". Genomics, Vol 54, pp. 361–378, 1998.*
D.B. Brunson, et al., "Investigation of the Causal Mutation for Malignant Hyperthermia in Black Labrador Retrievers," Canine Practice 23(1):48, 1998 (Abstract).
K. Hogan, et al., "Molecular Biology of Canine Malignant Hyperthermia (3)," VIII International MH Conference 9/96 (Abstract).
M.C. Roberts, et al., International Society for Animal Genetics, Jul. 2000 (Abstract).

* cited by examiner

Primary Examiner—Gary Benzion
Assistant Examiner—Jeanine Goldberg
(74) Attorney, Agent, or Firm—Quarles & Brady LLP

(57) ABSTRACT

A method of determining whether a canine is susceptible to canine malignant hyperthermia is disclosed. In one embodiment, this method comprises the step of obtaining a nucleic acid sample from a canine and examining the DNA sample for the presence or absence of a T1640C mutation, wherein the presence of the mutation indicates that the canine is susceptible to canine malignant hyperthermia.

6 Claims, 4 Drawing Sheets

```
                       527
mhdogexon15    SLIRGNRSNC ALFSTNLDWL ASKLDRLEAS S
dogexon15      SLIRGNRSNC ALFSTNLDWL VSKLDRLEAS S
humexon15      SLIRGNRSNC ALFSTNLDWL VSKLDRLEAS S
ratexon15      SLIRGNRTNC ALFSTNLDWL VSKLDRLEAS S
rabexon15      SLIRGNRANC ALFSTNLDWV VSKLDRLEAS S
pigexon15      SLIRGNRANC ALFSNNLDWL VSKLDRLEAS S
```

FIG. 3

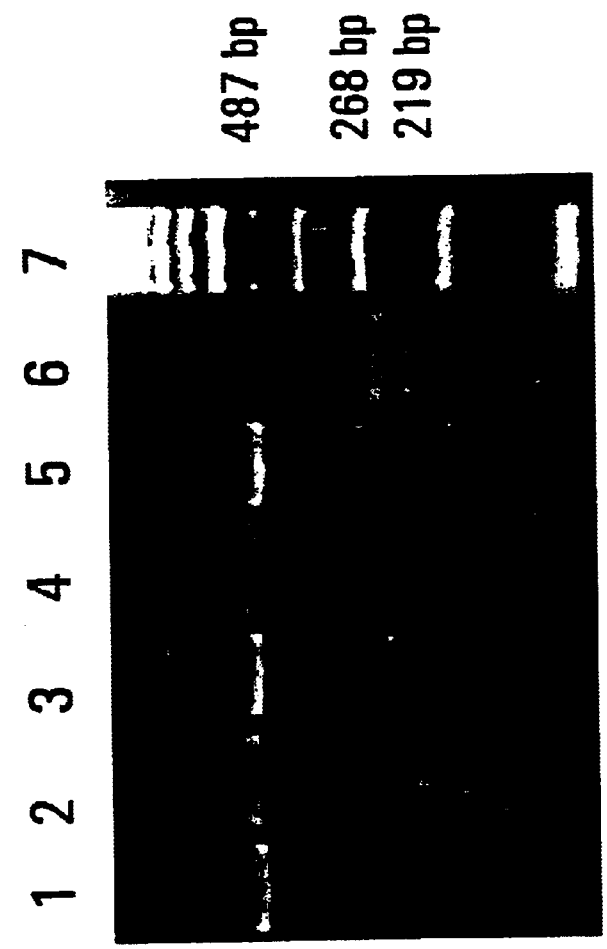

SEQUENCE LISTING

<160> NUMBER OF SEQ ID NOS: 20

<210> SEQ ID NO 1
<211> LENGTH: 31
<212> TYPE: PRT
<213> ORGANISM: Dog

```
<220> FEATURE:
<221> NAME/KEY: SITE
<222> LOCATION: (21)
<223> OTHER INFORMATION: mutation: from Valine to Alanine.

<400> SEQUENCE: 1

Ser Leu Ile Arg Gly Asn Arg Ser Asn Cys Ala Leu Phe Ser Thr Asn
 1               5                  10                  15

Leu Asp Trp Leu Ala Ser Lys Leu Asp Arg Leu Glu Ala Ser Ser
            20                  25                  30

<210> SEQ ID NO 2
<211> LENGTH: 31
<212> TYPE: PRT
<213> ORGANISM: Dog

<400> SEQUENCE: 2

Ser Leu Ile Arg Gly Asn Arg Ser Asn Cys Ala Leu Phe Ser Thr Asn
 1               5                  10                  15

Leu Asp Trp Leu Val Ser Lys Leu Asp Arg Leu Glu Ala Ser Ser
            20                  25                  30

<210> SEQ ID NO 3
<211> LENGTH: 31
<212> TYPE: PRT
<213> ORGANISM: Homo sapiens

<400> SEQUENCE: 3

Ser Leu Ile Arg Gly Asn Arg Ser Asn Cys Ala Leu Phe Ser Thr Asn
 1               5                  10                  15

Leu Asp Trp Leu Val Ser Lys Leu Asp Arg Leu Glu Ala Ser Ser
            20                  25                  30

<210> SEQ ID NO 4
<211> LENGTH: 31
<212> TYPE: PRT
<213> ORGANISM: Rat

<400> SEQUENCE: 4

Ser Leu Ile Arg Gly Asn Arg Thr Asn Cys Ala Leu Phe Ser Thr Asn
 1               5                  10                  15

Leu Asp Trp Leu Val Ser Lys Leu Asp Arg Leu Glu Ala Ser Ser
            20                  25                  30

<210> SEQ ID NO 5
<211> LENGTH: 31
<212> TYPE: PRT
<213> ORGANISM: Rabbit

<400> SEQUENCE: 5

Ser Leu Ile Arg Gly Asn Arg Ala Asn Cys Ala Leu Phe Ser Thr Asn
 1               5                  10                  15

Leu Asp Trp Val Val Ser Lys Leu Asp Arg Leu Glu Ala Ser Ser
            20                  25                  30

<210> SEQ ID NO 6
<211> LENGTH: 31
<212> TYPE: PRT
<213> ORGANISM: Pig

<400> SEQUENCE: 6

Ser Leu Ile Arg Gly Asn Arg Ala Asn Cys Ala Leu Phe Ser Asn Asn
 1               5                  10                  15
```

Leu Asp Trp Leu Val Ser Lys Leu Asp Arg Leu Glu Ala Ser Ser
            20                  25                  30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 96-115.

<400> SEQUENCE: 7
cctcgacatc atgggtgacg                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 842-823.

<400> SEQUENCE: 8
tagtagacaa gtctgcgctg                                            20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(21)
<223> OTHER INFORMATION: Human RYR bases 698-718.

<400> SEQUENCE: 9
tgtggaacat gaaccccatc t                                          21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 1052-1483.

<400> SEQUENCE: 10
ttgctctgct tctcctcgtg                                            20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 1342-1361.

<400> SEQUENCE: 11
ttcatcaagg gcctggacag                                           20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(21)
<223> OTHER INFORMATION: Human RYR bases 2101-2081.

<400> SEQUENCE: 12
tccaccatca cctcaaagta c                                         21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 5931-5950.

<400> SEQUENCE: 13
ggagtatttc tgtgaccaag                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 6686-6667.

<400> SEQUENCE: 14
gggtgttggt agaagacttt                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 6595-6614.

<400> SEQUENCE: 15
ctggtgatcg tgcagatggg                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)

```
<223> OTHER INFORMATION: Human RYR bases 7396-7377.

<400> SEQUENCE: 16
ggtcgatcaa ggcagcatag                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 7093-7112.

<400> SEQUENCE: 17
tacctggact tcctgcgctt                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial
      Sequence:oligonucleotide
<221> NAME/KEY: misc_feature
<222> LOCATION: (1)..(20)
<223> OTHER INFORMATION: Human RYR bases 8009-7990.

<400> SEQUENCE: 18
aactcgttaa ggatcccgac                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 19
tggtcctgaa ctgtattgac                                               20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 20
cgtgcttgtc caggaggg                                                 18
```

ASSAY FOR PROPENSITY FOR CANINE MALIGNANT HYPERTHERMIA

CROSS-REFERENCE TO RELATED APPLICATION

STATEMENT REGARDING FEDERALLY SPONSORED RESEARCH OR DEVELOPMENT

BACKGROUND OF THE INVENTION

Malignant hyperthermia (MH), a pharmacogenetic disorder of skeletal muscle elicited by exposure to volatile anesthetics and depolarizing muscle relaxants, is well recognized in humans and pigs, although a number of definite episodes have also been reported in dogs.[1,2,3,4,5,6,7] When given these agents, MH susceptible (MHS) dogs exhibit tachycardia, hyperthermia, elevated carbon dioxide production, and death if the anesthetic is not discontinued. Specific interventions, including use of the calcium release channel antagonist dantrolene,[8,9] are efficacious in reversing signs of the canine syndrome. In most reports of MH in dogs metabolic acidosis is moderate and muscle rigidity is minimal, in contrast to the severity of both in the swine or human condition. Many additional accounts of episodes resembling MH in dogs within the peri-operative interval,[10,11,12,13] during exertion,[14,15,16,17] or other chemical exposures[18] have been published. Monitoring and laboratory investigations in these descriptions are scant, and uncertainties persist regarding the incidence of canine MH, as well as its relation to other disorders in the dog, and to MH in other species.

To resolve these issues, Thomas E. Nelson assembled a pedigree for in vivo halothane/succinylcholine challenge and in vitro contracture testing (IVCT), beginning with a Doberman-German Shepherd-Collie mixed breed progenitor from a colony maintained by the late Dr. Barry Reynolds at the University of Saskatchewan.[19] Members of the pedigree produced by the mating of this dog to an MHN (MH Normal) Labrador Retriever dam were challenged under well-controlled anesthetic dosing regimens. Contemporary monitors and serial laboratory assays were used to discriminate features shared with human and swine MH from those that were distinct, and to establish the predictive value of the IVCT in a third species. Subsequently, a male subject in these experiments became the propositus of a second colony bred for molecular genetic diagnosis. His mates and all viable descendants were IVCT phenotyped to ascertain MH status, and in vivo halothane/succinylcholine challenge tests were simultaneously conducted in all dogs from 4 of the 6 sibships. Because swine and many human probands are predisposed to MHS by mutations in the calcium release channel gene (RYR1),[20] co-segregation was sought between inheritance of the canine MHS trait and RYR1 as a candidate locus. Initial experiments ruled out the RYR1 mutation shared between all MHS swine (R614C) and 2–7% of human MHS (R615C) pedigrees.[21]

SUMMARY OF THE INVENTION

In one embodiment, the present invention is a method of determining whether a canine is susceptible to canine malignant hyperthermia. This invention is desirable because one would wish to test for this potentially life-threatening condition prior to surgery on a pet or valuable breeding or research animal.

The method preferably comprises the step of obtaining a nucleic acid sample from a canine and examining the sample for the presence or absence of a T1640C mutation, wherein the presence of the mutation indicates that the canine is susceptible to canine malignant hyperthermia. Preferably, the nucleic acid sample is a genomic DNA sample.

In another embodiment, the present invention is the method as described above wherein the step of examining the sample for the presence or absence of a T1640C mutation comprises amplifying a portion of the canine RYR1 locus and examining the amplified product for the presence of the mutation. Preferably, the method further comprises the step of digesting the amplification product with a restriction endonuclease, most preferably Mscl.

It is an object of the the present invention to provide a method of determining whether a canine is susceptible to canine malignant hyperthermia.

Other objects, features and advantages of the present invention will become apparent after one has reviewed the specifications, claims and drawings.

DESCRIPTION OF THE DRAWINGS

FIG. 3: Amino acid comparison of exon 15 in dog and four other species. The MHS mutation is highlighted. The compared sequences begin at amino acid number 527 as indicated.

FIG. 4: PCR-RFLP analysis of homozygous wild-type (#4-5405), heterozygous MHS (#4-5404), and homozygous mutant (#5-5443) pups. Primers RYR1-14.F and RYR1-16A.R were used to amplify the 487 bp fragments which are shown uncut in lanes 1,3 and 5 from left to right. Lane 7 is a 100 bp ladder. The MHS mutation creates a new Mscl recognition site enabling analysis for the mutation. If the dog has two copies of the normal allele at position 1640, the digest will show only the 487 bp product (lane 2). If the dog has a single mutant allele at position 1640, the PCR product will have one allele digested and the other not, to show three size products on the gel; 487 bp, 268 bp and 219 bp (lane 4). If the dog is homozygous for the MHS mutation no 487 bp fragment will be seen, with the PCR products from both chromosomes fully digested to the 268 bp and 219 bp fragments (lane 6).

DESCRIPTION OF THE INVENTION

Figure 1:
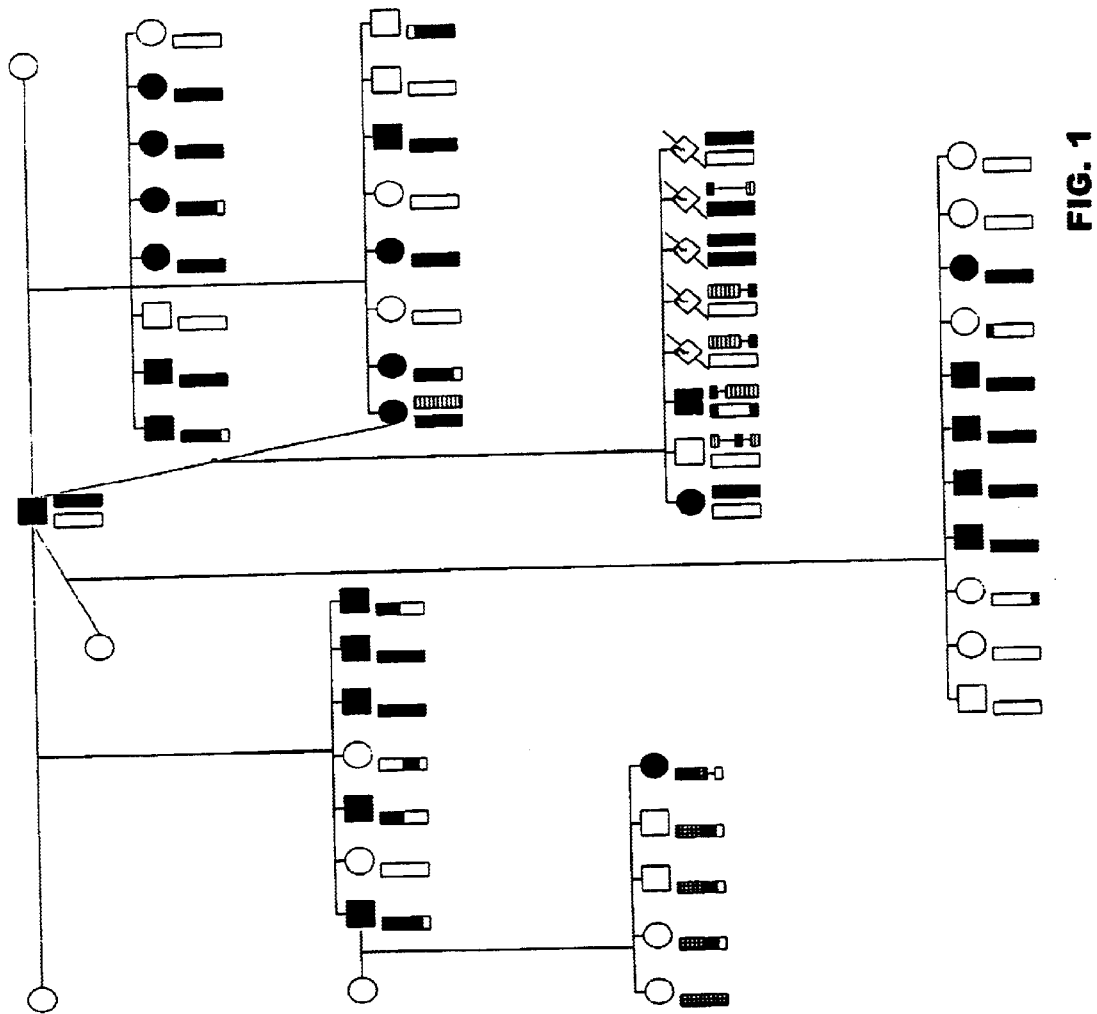
FIG. 1: The canine MH colony. MHS dogs are represented by black; MHN dogs are represented by white; dogs of unknown phenotype are represented by a question mark in a diamond. #A-10's haplotype is indicated in the box. Bars for the offspring are only shown for A-10's chromosome. MHS or MHN diagnoses were made by in vivo halothane/succinylcholine clinical challenge and IVCT. Genotyping with CFA01 markers was performed as described in the Examples.

To determine the molecular basis of canine MH, a breeding colony was established with a male mixed breed MH susceptible (MHS) dog that survived an in vivo halothane/succinylcholine challenge. He was mated to three unaffected females to produce four litters, and back-crossed to an affected daughter to produce one litter. One of his MH susceptible (MHS) sons was mated to an unaffected female to produce an additional litter. Forty-seven dogs were phenotyped with an in vitro contracture test (IVCT), and diagnosed MHS or MH normal (MHN) based on the North American IVCT protocol. Nine micro-satellite markers in the vicinity of RYR1 on canine chromosome 1 (CFA01) were tested for linkage to the MHS phenotype. Mutational analysis in 2 MHS and 2 MHN dogs was performed with direct sequencing of PCR products and of cloned fragments which represent frequently mutated human RYR1 regions. A restriction fragment length polymorphism was chosen to detect the candidate mutation in the pedigree at large.

Pedigree inspection revealed that MH susceptibility in this colony was transmitted as an autosomal dominant trait. FH2294, the marker closest to RYR1, was linked to MHS at a $\theta=0.03$ with a LOD score of 9.24. A T1640C mutation that gives rise to an alanine for valine substitution of amino acid 547 in the RYR1 protein generated a maximum LOD score of 12.29 at $\theta=0.00$. All dogs diagnosed MHS by IVCT are heterozygous for the mutation, and all MHN dogs are homozygous for the T1640 allele.

These results indicate that autosomal dominant canine MH is caused by a mutation in the gene encoding the skeletal muscle calcium release channel, and that the MHS trait in this pedigree of mixed breed dogs is in perfect co-segregation with a RYR1 V547A mutation.

In one embodiment, the present invention is a method of determining whether a canine is susceptible to canine malignant hypothermia. Preferably, the method comprises the steps of obtaining a nucleic acid sample from a canine, preferably a genomic DNA sample, and examining the sample for the presence or absence of a T1640C mutation. The presence of the mutation indicates that the canine is susceptible to canine malignant hypothermia.

By "T1640C mutation" we mean an alanine to valine change at amino acid 547 in the RYR1 protein. For information regarding the RYR1 region, one of skill in the art may consult reference 23, Priat, 1998 (incorporated by reference).

The presence of this mutation may be determined in many ways known to one of skill in the art. Genomic DNA of a canine subject may be extracted from any tissue, preferably whole blood, muscle sample or buccal smear, as described below in the Examples. One could employ PCR primers, described in Table 1 of the examples, to amplify the fragment between exons 14 and 16 (RYR1-1416) from the genomic DNA template. The candidate mutation creates a restriction enzyme recognition sequence for the restriction enzyme MscI and enables its detection by PCR followed by enzyme digestion. The Examples describe a preferred method for MscI digestion.

Of course, one may also elect numerous other ways to evaluate a canine nucleic acid sample for the presence of the T1640C mutation. For example, one could directly sequence the PCR amplification product. One would typically make use of primers designed to amplify the region including the mutation. Preferable primers are described in Table 1.

One could also use other methods of identifying single point mutations, such as flap endonculease cleavage methods (INVADER Third Wave, Madison, Wis.). Other detection methods are described in the following U.S. patents, all incorporated by reference: Lillicrap, et al., U.S. Pat. No. 6,251,632; Andersson, et al., U.S. Pat. No. 6,210,897; and Aguirre, et al., U.S. Pat. No. 6,201,114.

Another embodiment of the present invention is a kit to useful for determining whether a canine has propensity for malignant hypothermia. In one embodiment, this kit comprises suitable primers, preferably primers capable of amplifying RYRI3 and RYRI 1416, and a restriction enzyme capable of differential cleavage, preferably MscI.

One might also include restriction enzyme buffer and amplification enzymes and buffers.

EXAMPLES

Materials and Methods

MH Dog Breeding Colony

All investigations were carried out with the approval of the Institutional Animal Care and Use Committees of the University of Wisconsin, Madison, Wis.; Wake Forest University, Winston-Salem, N.C.; and the University of Texas, Houston, Tex. To assemble the breeding colony, a MHS Doberman-German Shepherd-Collie-Labrador Retriever mixed breed sire was selected from a previously reported kindred,[19] and out-crossed to three unrelated, mixed breed MHN females producing 4 litters, and back-crossed to one MHS daughter producing one litter. An MHS male offspring (#6-5450) was also mated to an unrelated mixed breed MHN female. These pairings produced 34 F1 and 13 F2 sibs. Including all parents, a total of 52 dogs were available for genotyping, of which 47 were phenotyped by IVCT.

In vivo Halothane/succinylcholine Challenge Testing

Dogs were anesthetized with pentobarbital 25 mg/kg i.v., the trachea intubated and the lungs mechanically ventilated with 30% $O_2$ and 70% $N_2O$ at volumes sufficient to maintain end-tidal $CO_2$ at 35–40 mm Hg partial pressure. After removal of gracilis muscle bundles for contracture testing, the femoral artery was cannulated for sample collection and arterial pressure transduction. Halothane (2% inspired in oxygen) and succinylcholine (0.3 mg/kg body weight IV) were administered as previously described,[19] and dantrolene (0.2 mg/kg body weight IV every 3 minutes to a total dose of 3.0 mg/kg) administered when life-threatening tachydysrhythmias, acidosis or hyperthermia developed. Thirty-one dogs were tested with in vivo challenge anesthetics, including all parents, and all dogs in sibships #3 through #6. Sixteen pups in sibships #7 and #9 did not undergo in vivo challenge testing. By the time these dogs were large enough for IVCT assays, the correlation between MHS and IVCT was sufficiently established to preclude the additional costs and euthanasias of further in vivo challenges. Five pups from the back-cross lifter of eight were either stillborn, or died shortly after birth, precluding ascertainment of the MH phenotype by any method.

In vitro Contracture Testing (IVCT)

Specimens of gracilis muscle were biopsied immediately preceding the in vivo test using protocols approved by North American MH Group for human MH diagnosis.[19,22] Fasicle viability for contracture testing was assessed before exposure to caffeine and halothane by electrically-evoked contracture tensions. For all fasicles from all MHS and MHN dogs the contracture tension averaged 8.24±0.24 g. Three tests were performed on biopsied muscle fasicles: increment in contracture tension (g) in the presence of 3% halothane; caffeine specific concentration (mM) (CSC) required to generate a 1 g isometric contracture; and the halothane caffeine specific concentration (mM) (HCSC) reflecting a measure identical to the CSC but performed in the presence of 1% halothane. Bundles from all dogs were tested in triplicate for the 3% halothane test, and were triply replicated in the majority for the CSC and HCSC as permitted by the availability of viable fasicles.

Genomic DNA Isolation

Genomic DNA of each canine subject was extracted either from EDTA preserved whole blood in dogs undergoing IVCT, or from frozen muscle in the non-viable back-cross animals, using the Puregene DNA isolation kit (Gentra Systems, Minneapolis, Minn., USA).

Selection of DNA Markers

Canine RYR1 was located on chromosome 1 (CFA01) by radiation hybrid (RH) mapping.[23] Polymorphic microsatellite markers from CFA01 were selected from an integrated physical-genetic linkage map with appended polymerase chain reaction (PCR) primers specific for each marker locus.[24] CFA01 marker order in the region is REN143K19-RYR1-FH2294-FH2326-C01.164-FH2309-C01.251-C01.246-FH2313-FH2016, spanning 90.7 cM and 639.6 cR.

Genotyping

PCR reactions containing 12.5 ng DNA, PCR Buffer (Qiagen, Inc., Valencia, Calif., USA), 1.5 mM $MgCl_2$, 5 pmol each of specific forward and reverse primers, 25 µM each of dCTP, dGTP, and dTTP, 6.25 µM dATP, 0.125 µCi [$\alpha$-$^{33}$P] dATP and 0.3 units HotStarTaq polymerase (Qiagen, Inc., Valencia, Calif., USA) in a final volume of 15 µl were performed in 96 well plates with initial denaturation at 94° C. for 15 minutes; 30 cycles of 92° C. for 30 seconds, 56° C. for 30 seconds, and 72° C. for 30 seconds; and a final extension at 72° C. for 5 minutes using a PTC-100 thermocycler (MJ Research, Inc., Incline Village, Nev., USA). The reaction products were observed by electrophoresis through 5% acrylamide denaturing gels on BioRad SequiGen GT 38×50-cm plate sequencing gel units (BioRad Laboratories, Hercules, Calif., USA), and alleles sized by comparison to an M13 sequence ladder after autoradiography.

RYR1 cDNA Synthesis mRNA was isolated from 200 mg of skeletal muscle harvested from 2 MHN (#3-5346 and #9-5504) and 2 MHS (#3-5348 and #9-5507) dogs using the Micro Fast Track 2.0 mRNA isolation kit (Invitrogen, Carlsbad, Calif., USA). First strand cDNA was synthesized using 1.0 µl of mRNA, either 75 ng random hexamers or 1.5 µM RYR1-6, reverse primer (Table 1.), 2.5 mM $MgCl_2$, 0.5 mM dNTPs, 10 mM DTT and 100 units BRL Superscript II Reverse Transcriptase (Life Technologies, Rockville, Md., USA).

RYR1 cDNA Sequencing—PCR Templates

Two regions of the RYR1 cDNA were selected for sequencing based on the frequency of previously identified mutant sites in humans and swine.[20] Region I containing bases #22-1982 was sequenced by overlapping PCR products RYR1-1, RYR1-2 and RYR1-3 (Table 1). Region II containing bases 5946–7927 was sequenced by overlapping PCR products RYR1-4, RYR1-5 and RYR1-6 b (Table 1). PCR primers designed to reflect consensus pig, human and rabbit sequences are shown in Table 1. PCR amplification of RYR1 cDNA templates used 0.8 µg cDNA in 1.0 µl, 200 nM of each primer, 5.0 µl of buffer (Qiagen, Inc., Valencia, Calif., USA), with 1.5 mM $MgCl_2$, 200 µM dNTPs and 0.5 units HotStarTaq (Qiagen, Inc., Valencia, Calif., USA) in a 50 µl PCR reaction. The cycling conditions were an initial denaturation at 94° C. for 15 minutes; 30 cycles of 94° C. for 30 seconds, 56° C. for 30 seconds, 72° C. for 30 seconds; and a final extension at 72° C. for 5 minutes. PCR products were sequenced in the forward and reverse directions using an ABI 377 by the Advanced Genetic Analysis Center (AGAC) of the University of Minnesota.

RYR1 cDNA Sequencing—Cloned Templates

Because disproportionate representation by PCR amplification may conceal heterozygous alleles on direct sequencing, RYR1-3 PCR products from the MHS dog #3-5348 were also cloned. PCR products were ligated into Invitrogen vector pCR-TOPO, transformed into *E. coli* competent cells (Invitrogen, Carlsbad, Calif., USA), and plated on LB/Ampicillin plates. Twenty two colonies were picked for PCR analysis.

Sequencing RYR1—Genomic DNA

PCR primers RYR1-14.Forward (SEQ ID NO:19) and RYR1-16.Reverse (SEQ ID NO:20) (Table 1) were designed to amplify the fragment between exons 14 and 16 (RYR1-1416) from genomic DNA templates based on the canine sequence of PCR product RYR1-3, and the known intron/exon boundaries of human RYR1. The reaction consisted of 25 ng genomic DNA, 40 µM dNTPs, 1.5 µl PCR buffer with 1.5 mM $MgCl_2$ (Qiagen, Inc., Valencia, Calif., USA), 0.3 units HotStarTaq (Qiagen, Inc., Valencia, Calif., USA), and 0.67 µM of each primer in each 15 µl reaction, with conditions otherwise as described above. Genomic RYR1 PCR products were sequenced using the RYR1-14. Forward (SEQ ID NO:19) primer at the AGAC.

PCR-restriction Enzyme Digestion

The candidate mutation creates a recognition sequence (5' . . . TGG<u>C</u>CA . . . 3') for the restriction enzyme Mscl (New England Biolabs, Beverly, Mass., USA) enabling its detection in the pedigree by PCR followed by enzyme digestion. PCR primers RYR1-14.Forward (SEQ ID NO:19) and RYR1-16.Reverse (SEQ ID NO:20) (Table 1) were used to amplify the genomic segment containing exon 14 to exon 16 (product RYR1-1416) from all 52 colony dogs, and from 24 unrelated dogs with no known history of MH or exercise intolerance. For each digestion, 7.5 µl of genomic PCR product was incubated with 1.5 units of Mscl in a total reaction volume of 20 µl containing 2.0 µl NEB buffer 4 (New England Biolabs, Inc, Beverly, Mass., USA) at 37° C. for 2 hours. The digestion products were size-separated by electrophoresis in 2.5% agarose in TAE buffer, and observed by staining with ethidium bromide.

Statistics

The pedigree depicted in FIG. 1 was constructed with Cyrillic2 software.[25] Subject genotypes were entered in Cyrillic2, and exported to MLINK[26] and CRIMAP[27] for analysis. The most probable mechanism of inheritance was estimated using a likelihood ratio comparing autosomal dominant and recessive descent. Linkage between MHS and each marker was tested in MLINK with parameters selected for autosomal dominant inheritance at full penetrance. Loci were ordered using the TWOPOINT option of CRIMAP for calculation of LOD scores and recombination fractions (q) between CFA01 markers. BUILD and ALL options were used to resolve the most probable order of markers and MHS. This order was verified by comparing the log of the likelihoods of the original order of paired loci to their reversed order using the FLIPS_N option. The map diagram was prepared using MapCreator (AJD Computing).

Results

In vivo Halothane/Succinylcholine Challenge Test Results

The premonitory sign of MH in this mixed breed pedigree is hypercarbia and increased carbon dioxide production (78.5±28 ml/min/kg) (X±S.D.) occurring as early as 10 minutes after exposure to halothane and succinylcholine, followed by tachycardia (178±29 beats/min) and hyperthermia (40±1.69° C.) within the first hour.[19] Dantrolene administration rapidly reverses biochemical and clinical evidence of the syndrome. Arterial blood lactate does not differ between challenged MHN and MHS dogs, nor is skeletal muscle rigidity a prominent feature of the triggered condition.

IVCT Results

Mean contracture responses to 3% halothane of muscle fasicles from dogs that did not develop clinical MH during in vivo challenge exhibited less than 0.2 g tension in all cases (0.02g±0.05), whereas muscle from each of the MHS dogs exceeded 0.2 g isometric contracture (0.83g±0.43). Eighteen of 23 MHN dogs exhibited no contracture in any fasicle in the presence of 3% halothane. The mean CSC was less than 6.0 mM caffeine (3.12 mM±1.36) in all 24 dogs that were MHS by in vivo challenge and 3% halothane IVCT. Nineteen of 23 dogs MHN by in vivo challenge and 3% halothane required a CSC of greater than 6.0 mM on mean (13.06 mM±5.51); in four MHN dogs the mean CSC was less than 6.0 mM (#3-5271 (4.40), #3-5344 (3.69), #3-5350 (5.62), #7-5478 (5.20)). Limited amount and viability of tissue precluded HCSC testing in 3 MHN and 2 MHS dogs diagnosed by in vivo challenge and 3% halothane contracture. The mean HCSC of 17 of 20 MHN dogs was greater than 2.0 mM caffeine (3.10 mM±0.77); in 3 dogs it was less (#3-5271 (1.73), #9-5503 (1.79), #9-5504 (1.99). The mean HCSC was less than 2.0 mM in 21 of 22 MHS dogs (0.85 mM±0.39), with the exception of dog #4-5403 (2.84 mM).

Of the 47 F1 and F2 offspring in the colony, 23 dogs are MHS, 19 are MHN, and 5 in the back-cross sibship are indeterminate (FIG. 1). Thirteen MHS pups are males and 10 are females suggesting that if a gender bias exists in the canine MHS syndrome the magnitude of its effect is small. Both affected and unaffected dogs are found in each of the 6 litters, ranging from 1 of 5 dogs MHS in sibship #9, to 6 of 8 dogs MHS in sibship #4. Because the probability of two affected parents producing an unaffected offspring is zero under the assumption of recessive inheritance, presence of the MHN pup (#5-5439) within the back-cross sibship excludes the possibility of recessive inheritance in this pedigree as ascertained by IVCT. Furthermore, a distribution compatible with autosomal recessive descent would require that the unrelated dams of all litters be heterozygous for MHS, with a homozygous MHS sire. Rather, heterozygosity by random selection of dams is unlikely in light of the presumed rarity of the phenotype.

Genotype Results

CFA01 marker haplotypes in the canine MH pedigree are depicted in FIG. 1. The propositus #A-10 is heterozygous for markers REN143K9, FH2294, C01.164, FH2309, C01.251 and FH2313, with two, four, two, five, three, and seven alleles segregating in the family, respectively. The propositus haplotypes are a-e-a-c-c-c and b-d-b-a-b-e in marker order REN 143K9-FH2294-C01.164-FH2309-C01.251-FH2313. For non-recombinant dogs, the a-e-a-c-c-c propositus haplotype segregates with the MHS trait, while the b-d-b-a-b-e propositus haplotype segregates with MHN.

The MHS propositus is an ab heterozygote for the marker REN143K9, whereas his MHN mates are bb homozygotes. Each of the offspring exhibiting the ab REN143K9 genotype are MHS, with the exception of MHN #7-5483, indicating that a single recombinant event between REN143K9 and the MHS locus occurred in this individual. Similarly, the e allele of FH2294 segregates with MHS in every instance but one. The exception is individual #3-5350 with evidence for recombination between the FH2294 marker e allele and the MHS phenotype. The MHS mother of the back-cross sibship (#3-5347) carries one copy of chromosome 1 with an FH2294 e allele linked to MH from the propositus. Her second chromosome 1 contains an FH2294 e allele unlinked to MH from her mother (#3-5271). The offspring of her pairing with the propositus at the MH locus are: homozygous with both MHS-linked FH2294 e alleles from the propositus chromosome (#5-5443, #5-5444); heterozygous with the MHS-linked FH2294 e allele from either the father (#5-5440) or the mother (#5-5438, #5-5445); or homozygous for the unlinked FH2294 e allele from the mother and the d allele from the unlinked propositus chromosome 1 (#5-5439, #5-5441, #5-5442).

Within this panel of CFA01 markers MLINK calculations reveal that FH2294 is most closely linked to MHS with a maximum LOD score at q=0.05 of 8.9 (Table 2.). Under the CRIMAP TWOPOINT option, MHS and FH2294 are linked with a maximum LOD score at q=0.03 of 9.42. REN143K9 is linked to MHS at q=0.05, LOD 8.24, and C01.164 at q=0.07, LOD of 8.16, with no evidence for recombination between FH2294 and CO 1.164 in this pedigree. No other CFA01 markers were linked to MHS with a LOD>3.0 at q<0.1 in MLINK.

Figure 2:
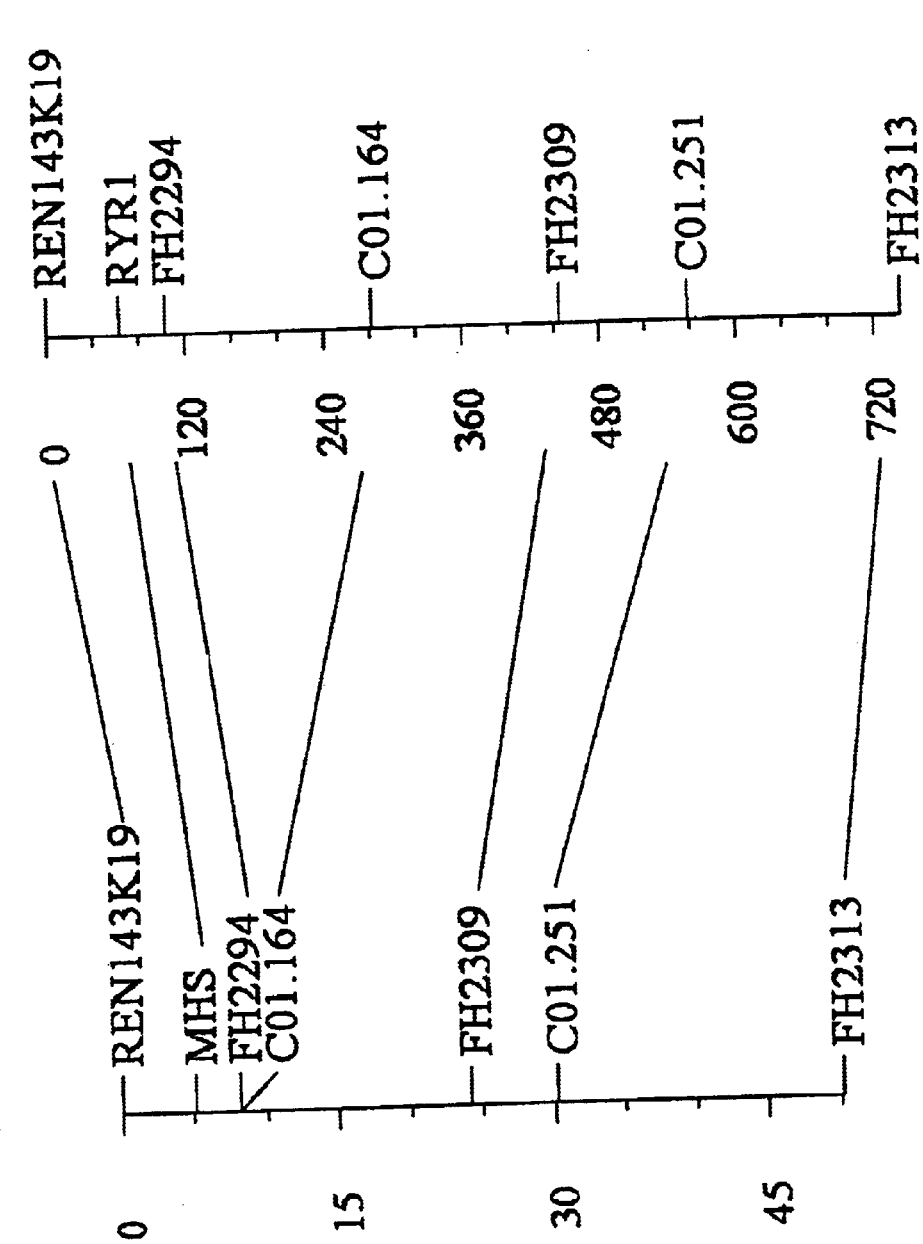
FIG. 2: A comparison of CFA01 maps constructed with linkage data from our MH colony dogs and the whole genome RH panel.[24] The map was made with the MapMaker program. The MH colony linkage map represents our data measured in centiMorgans. The radiation hybrid map was assembled in accord with published distances measured in centiRays.[24]

The BUILD and ALL options of CRIMAP were used to construct a genetic linkage map of CFA01 incorporating the MHS locus, presented for comparison with the published RH map[24] in FIG. 2. Although primarily designed for use in mapping co-dominant loci, CRIMAP may also be of value for ordering expressed disease loci providing the genotypes are known. Only pups arising from an out-cross of an MHS to MHN subject are informative for CRIMAP analysis; failure to distinguish backcrossed MHS heterozygotes from MHS homozygotes precludes their entry into analysis. The out-crossed data was unable to resolve two possible orders: REN143K9-MHS-C01.164-FH2294-FH2309-C01.251-FH2313; vs. REN143K9-MHS-FH2294-C01.164-FH2309-C01.251-FH2313. FLIPS_N analysis verified that both were equally likely, but that other than the ambiguous positions of markers FH2294 and C01.164, the remainder of the alignment is most probable. The finding that two flanking markers (REN143K9, FH2294) are recombinant for two different offspring (#7-5483, #3-5350) provides strong evidence that the mutant MHS locus is interposed. The MHS locus on the linkage map is in the same proximal-telomeric position as the RYR1 locus on the canine RH map (FIG. 2), and marker order is identical for both, although the linkage map was assembled from just 42 informative meioses in the MH pedigree, and distances between markers are therefore estimates.

Mutational Analysis Results

Two regions of the RYR1 gene bracketing 21 human mutations associated with MHS[20] were selected for a canine mutation search by direct sequencing. Region I extends from nucleotides 22 to 1982, corresponding to amino acids 7–660 of the sarcoplasmic foot of the calcium release channel. Region II spans nucleotides 5946 to 7927 encoding amino acids 1982–2642. Analysis of RT-PCR product sequence from MHS dog #3-5348 disclosed a C for T polymorphism at nucleotide 1640 in exon 15, consistent with heterozygosity of the MHS genotype. The T1640C substitution was identified in replicate RNA isolations from the affected dog muscle, in replicate reverse transcriptase PCR products from different #3-5348 cDNA templates, and in bi-directional sequencing of these PCR products. PCR products encompassing this region from #3-5348 were independently cloned and sequenced. The mutant T1640C allele was found in 6 of 22 clones, with 16 of 22 representing the wild-type T1640 allele, indicating that the polymorphism represents a genetic substitution rather than an error in amplification or sequencing.

The T1640C mutation results in the exchange of an alanine for valine at amino acid residue 547 in RYR1 exon 15. The nucleotide sequences of canine regions I and II have been submitted to GenBank (accession #A302128 and #AF302129, respectively). Canine and human nucleotide sequence in regions I and II reveal >91% identity, with >95% homology between derived protein sequences (Table 3.). A comparison of dog, human, rat, rabbit and pig amino acid sequences surrounding the V547A site demonstrates that the valine 547 is phylogenetically conserved (FIG. 3). Because the T1640C mutation creates a recognition site for restriction enzyme Mscl, each animal in the pedigree could be screened for the mutation using PCR-RFLP analysis. FIG. 4 shows a representative agarose gel of Mscl digested PCR products for the three possible genotypes: the homozygous TT MHN wild-type (#4-5405) fragment is uncut at 487 bp in length; the homozygous CC mutant (#5-5443) product is fully digested to 268 and 219 bp fragments; all three fragment sizes are present in the digested PCR products of MHS dogs heterozygous for the T1640C substitution (#4-5404). Every dog diagnosed as MHS by the IVCT exhibits the mutation. All MHN dogs by IVCT and in vivo challenge have two copies of the normal T1640 allele, including MHN #3-5350 that is recombinant between the MH locus and the FH2294 e allele, and MHN #7-5483 that is recombinant between the MH locus and the REN143K9 a allele. In this canine MHS pedigree, at q=0.0 the maximum LOD score of the T1640C mutation with MHS is 12.29. None of 24 unrelated control dogs representing 48 chromosome 1 genotypes carry the T1640C substitution.

Discussion

Malignant hyperthermia in a dog was first reported in 1973.[1] No subsequent investigation has tested for linkage of the canine MH phenotype to candidate genes or anonymous DNA markers. Here we report that canine MH ascertained by in vivo halothane/succinylcholine clinical challenge and IVCT is tightly linked to markers in the near vicinity of RYR1, with a recombinant for each of the two markers most closely flanking the MHS/RYR1 locus. Moreover, an intragenic T1640C substitution in RYR1 exon 15, which generates a V547A mutation in the RYR1 peptide, is in perfect co-segregation with inheritance of the MHS trait. These findings, together with the absence of the V547A transition in a randomly selected group of control dogs, and prior recognition of the region as a mutational hotspot in human MH, suggest that the V547A mutation causes MH in this mixed breed dog colony.

Although MH-like events during exposure to anesthetics in dogs have been documented for nearly 30 years, in most of the previous reports monitoring was scant, clinical descriptions incomplete, and IVCTs were either not performed or were conducted according to non-standard protocols. Nevertheless, the diagnosis of MH based on clinical event, laboratory exposure to trigger anesthetics or IVCT appears clear and convincing in a purebred Pointer,[1] Greyhounds,[2,3] mixed breed Doberman Pinscher/German Shepherds,[5,6] a Labrador Retriever,[7] and a dog of unspecified breed.[4] Possible perioperative MH-like events have also been reported in a St. Bernard,[11] Greyhounds,[13] a Springer Spaniel,[15] and unspecified breeds,[10] but the available data is less persuasive for a diagnosis of true MH. In aggregate, the main features of the canine MH syndrome shared with humans and pigs include identical pharmacologic triggering agents, hypercarbia, hyperthermia, tachycardia, therapeutic efficacy of dantrolene and supportive measures, and death if untreated. Consistent with our observations, but in contrast to manifestations of the disorder in humans and pigs, lactic acidemia, metabolic acidosis, and extensor rigidity are absent in most cases and delayed in the remainder. Investigations comparing exercise performance in the normal dog and pig reveal superior canine oxidative metabolic capacity, cardiac output, acid-base and heat regulatory elements which may contribute to physiologic compensation during an acute trigger in a predisposed dog.[28] In turn, the more subtle canine MH presentation may underlie missed diagnoses in the past and failure to investigate the true incidence of MH in canine surgery to the present, particularly in the absence of continuous core temperature and end expiratory gas monitoring.

Despite the relative lack of rigidity which characterizes the canine MHS syndrome, precision of the IVCT for phenotypic assignment is well-preserved across species boundaries. Indeed the lower end of the range of mean generated contracture tension in 3% halothane customarily selected for human diagnosis[22] (i.e. 0.2 g) is sufficient to resolve the phenotype of every individual in our colony in comparison both to in vivo halothane/succinylcholine challenge, and to RYR1 mutational analysis. Parsimony of IVCT results between susceptible and non-susceptible dogs, and between susceptible and non-susceptible pigs and humans, points not only to a shared molecular pathology, but reaffirms the value of the IVCT as conventionally configured for establishing MHS genotype-phenotype correlations in future model organisms. Coupled with the results of controlled clinical exposure to trigger anesthetic agents, we believe these IVCT results leave little doubt that the phenotype under present investigation represents a true homolog of MH in a third species, thereby warranting molecular investigations.

While dogs also display stress or exercise-induced hyperthermia,[12,14,15,16] with many features in common with porcine stress syndrome (PSS), non-anesthetic triggers in MHS humans are extremely rare. PSS is triggered in MHS strains of pigs by exertion, excitement, hypoxia or high ambient heat corresponding to an MH trigger in the absence of exposure to anesthetics. In pigs PSS is often fatal while in dogs exercise-induced hyperthermia is rapidly reversible. In one Greyhound a non-standard, uncontrolled IVCT performed after recovery from canine stress syndrome was judged to be normal,[17] whereas in a Springer Spaniel the IVCT was positive.[15] No episodes of exercise intolerance or exertional hyperthermia have been observed in the MHS members of our colony. Species-specific differences in the fiber type composition of skeletal muscle may account in part for disparate susceptibilities to non-anesthetic stress syndromes. Human and pig muscle consists of Types I, IIA, IIB, and IIC fiber types.[29] Absence of the more highly glycolytic type IIB fibers in dog skeletal muscle[30] may account for decreased lactate accumulation, minimal rigidity during an anesthetic MH trigger, and the reduced incidence and rapid recovery from non-anesthetic exercise-induced hyperthermia. As a consequence of our genetic investigations, it will now be possible to test dogs with exercise-induced hyperthermia or canine stress syndrome for a casual MHS mutation with the aim of unraveling potential associations between the clinical disorders.

For over 100 millennia the dog has been under intense breeding pressure in selection of traits conjoined to the hunt.[31] Paradoxically it is the working and sporting breeds that appear to be at greatest MHS risk. Over 300 modern strains of dogs originating from a progenitor wolf pool[32] share many of the traits and disorders that afflict humans providing exceptional models for the investigation of genetic contributions to cellular physiology and pathology.[33] Very recently canine genetic linkage and radiation hybrid maps using polymorphic microsatellite markers have been developed in support of the Dog Genome Project.[23,24] These reagents in tandem with rigorous diagnosis and controlled mating based on a priori determinations of the MHS phenotype, enabled our identification of the canine MHS locus as the RYR1 gene on dog chromosome 1 (CFA01).

The sarcoplasmic reticulum ryanodine receptor (RYR1) (calcium release channel), and the closely opposed transverse tubule dihydropyridine receptor (DHPR) (voltage dependent calcium channel) are key components of the excitation-contraction coupling apparatus in skeletal muscle. Normal muscle contractility commences with DHPR a, subunit conformational changes during t-tubule depolarization coupled to gating of RYR1, and release of sarcoplasmic reticulum calcium stores into the myoplasm. The calcium release channel is a large (564,000 Da) homotetrameric protein with high and low affinity sites for the binding of ryanodine associated with open channel conductance and inactivation, respectively. Halothane, other volatile anesthetic agents, and caffeine release calcium from the sarcoplasmic reticulum membrane by activating the channel.[34] Succinylcholine elicits MH by indirect action on the t-tubule/SR triad secondary to non-physiologic depolarization at the surface neuromuscular junction. In MHS individuals, RYR1 opens for a longer interval than normal in the presence of triggering drugs, and excessive calcium is extruded into the sarcoplasm.[35] Elevated resting sarcoplasmic calcium concentrations activate muscle contraction, promoting ATP hydrolysis, accelerated metabolism and hyperthermia which typify an MH reaction.[35]

Human RYR1 consists of a 15,393 bp cDNA transcript, with 106 exons spanning 158 kb of genomic DNA encoding 5038 amino acids, making it one of the largest genes known.[36] Close inter-species similarity in the regions of RYR1 we have sequenced suggests that the dog skeletal muscle RYR1 homolog will be very similar in overall size and structure to the human gene (Table 3.). Linkage of MHS to RYR1 in pigs and humans was first reported in 1990,[34] with porcine MH traced to a RYR1 R615C mutation shortly thereafter.[37] In humans, 21 mutations encoding the sarcoplasmic "foot" region of the RYR1 protein near the amino terminus (region I) or central portion (region II) are thought to cause MHS and/or central core disease, with 1 MHS mutation near the C terminus.[20] Mutations in the $a_1$ subunit of the DHPR (CACNA1S)[38] and in carnitine palmitoyl transferase II (CPT2)[39,40] have also been associated with MH in humans lacking a co-existing clinical myopathy. Thus, porcine MH is genetically homogenous with no evidence for a second gene or mutation, while human MH is a genetically heterogenous syndrome arising from alterations in RYR1, CACNA1S, and other components of skeletal muscle calcium regulation. Because the present investigation is the first to report canine MH linkage, it is premature to speculate whether dog MH will be genetically homogenous or heterogenous.

A second feature differentiating MH in humans and pigs is the mechanism of inheritance. Porcine MH is invariantly transmitted as an autosomal recessive trait. In humans clear-cut autosomal dominant MHS has been described in a number of large pedigrees, although the majority of families with an MH proband are too small and inadequately characterized to specify with certainty. Inheritance of MHS in our colony of mixed breed dogs, with a single mutant copy of the RYR1 locus sufficient to confer the fully penetrant MHS phenotype, more nearly resembles the human syndrome in this regard. Predisposition to trigger on stress, and on first exposure to contraindicated anesthetics, suggests that the causal mutation is more disruptive of RYR1 function in the pig than in the human or dog. However, the opposite is more likely to be the case since a single mutant copy is incapable of manifesting the MHS recessive clinical trait in pigs, nor is the porcine MHS heterozygote reliably detected by IVCT. Because heterozygotes pass MHS to 50% of their offspring, canine MH is not restricted to single strains exhibiting a preponderance of recessive disorders sustained by highly ordered matings. Rather, all dog breeds are at potential MHS risk.

In our pedigree all MHS dogs by phenotype carry the T1640C genotype, and all MHN dogs lack the mutation. Taken alone this data is presumptive for causality of the MHS trait, but it is also plausible that the RYR1 T1640C substitution merely serves as a proxy polymorphism for a truly causal mutation elsewhere in RYR1 or in a nearby gene. Evidence against the latter hypothesis includes: linkage of the MHS trait to anonymous markers flanking RYR1; perfect co-segregation of MHS with T1640C incorporating two flanking recombinants; absence of the polymorphism in a randomly selected sample of control canine chromosomes; a consequent non-synonymous amino acid substitution; causality of RYR1 mutations for MHS in at least two other species; and occurrence of the mutation in a phylogenetically conserved region of RYR1 known to be a mutational "hotspot" for MHS in humans. Additional support for causality of the V547A mutation awaits detailed analysis of its functional correlates compared to normal in RYR1 binding assays, single channel recordings and whole cell expression of the mutant protein. Inevitably, these investigations will also yield a deeper understanding of E-C coupling and its disorders in a second laboratory organism.

In conclusion, MHS in a large, well-characterized canine pedigree segregates in perfect accord with inheritance of a V547A mutation in the RYR1 gene. These data represent both the first pharmacogenomic, and the first autosomal dominant syndrome found in humans and dogs to share a common molecular mechanism. The presence of the specific mutation may now be sought in other species and dog breeds exhibiting MH and related hyperthermic stress syndromes. Detection of the mutant allele by clinical challenge and IVCT suggests that the dog may be a useful model for the development of improved phenotypic detection of heterozygotes needed for human diagnosis and genetic investigations.

TABLE 1

List of primers for the overlapping PCR products used for sequencing.

| PCR Product | Forward Primer Sequence | Reverse Primer Sequence | Product Size (bp) |
|---|---|---|---|
| RYR1-1 | CCT CGA CAT CAT GGG TGA CG (SEQ ID NO:7) human bases 96–115 | TAG TAG ACA AGT CTG CGC TG (SEQ ID NO:8) human bases 842–823 | 746 |
| RYR1-2 | TGT GGA ACA TGA ACC CCA TCT (SEQ ID NO:9) human bases 698–718 | TTG CTC TGC TTC TCC TCG TG (SEQ ID NO:10) human bases 1502–1483 | 804 |
| RYR1-3 | TTC ATC AAG GGC CTG GAC AG (SEQ ID NO:11) human bases 1342–1361 | TCC ACC ATC ACC TCA AAG TAC (SEQ ID NO:12) human bases 2108–2088 | 759 |
| RYR1-4 | GGA GTA TTT CTG TGA CCA AG (SEQ ID NO:13) human bases 5931–5950 | GGG TGT TGG TAG AAG ACT TT (SEQ ID NO:14) human bases 6686–6667 | 755 |

TABLE 1-continued

List of primers for the overlapping PCR products used for sequencing.

| PCR Product | Forward Primer Sequence | Reverse Primer Sequence | Product Size (bp) |
|---|---|---|---|
| RYR1-5 | CTG GTG ATC GTG CAG ATG GG (SEQ ID NO:15) human bases 6595–6614 | GGT CGA TCA AGG CAG CAT AG (SEQ ID NO:16) human bases 7396–7377 | 801 |
| RYR1-6 | TAC CTG GAC TTC CTG CGC TT (SEQ ID NO:17) human bases 7093–7112 | AAC TCG TTA AGG ATC CCG AC (SEQ ID NO:18) human bases 8009–7990 | 916 |
| RYR1-1416 | TGG TCC TGA ACT GTA TTG AC (SEQ ID NO:19) | CGT GCT TGT CCA GGA GGG (SEQ ID NO:20) | 487 |

Table 2. Recombination frequencies (q) and LOD scores for MHS and CFA01 markers. Table 2a represents the LOD scores and recombination frequencies from the CriMap program. Table 2b represents the LOD scores and recombination frequencies from the LINKAGE program.

TABLE 2A

| | REN143K19 | | MHS | | FH2294 | | C01.164 | | FH2309 | | C01.251 | |
|---|---|---|---|---|---|---|---|---|---|---|---|---|
| | q | LOD | q | LOD | q | LOD | q | LOD | q | LOD | q | LOD |
| MHS | 0.05 | 8.83 | | | | | | | | | | |
| FH2294 | 0.07 | 7.65 | | | | | | | | | | |
| C01.164 | 0.12 | 6.44 | 0.07 | 8.16 | 0.00 | 12.04 | | | | | | |
| FH2309 | 0.25 | 2.35 | 0.23 | 2.63 | 0.20 | 4.42 | 0.16 | 4.86 | | | | |
| C01.251 | 0.18 | 3.05 | 0.11 | 4.82 | 0.17 | 4.32 | 0.09 | 5.79 | 0.06 | 8.97 | | |
| FH2313 | 0.31 | 1.18 | 0.27 | 1.52 | 0.30 | 1.78 | 0.31 | 1.18 | 0.23 | 3.53 | 0.20 | 2.96 |

TABLE 2B

| | REN143K19 | | FH2294 | | C01.164 | | FH2309 | | C01.251 | | FH2313 | |
|---|---|---|---|---|---|---|---|---|---|---|---|---|
| | q | LOD | q | LOD | q | LOD | q | LOD | q | LOD | q | LOD |
| MHS | 0.05 | 8.24 | 0.05 | 8.9 | 0.05 | 7.9 | 0.25 | 2.4 | 0.1 | 4.5 | 0.3 | 1.4 |

TABLE 3

Inter-species homology (%) of RYR1 nucleotide and protein sequence to that of the dog.
The MH-associated V547A mutation is in Region II, exon 15.

| | Nucleotide | Protein |
|---|---|---|
| Region I | | |
| Human | 92% | 97.5% |
| Pig | 93% | 97.6% |
| Rabbit | 91% | 97% |
| Region II | | |
| Human | 91.3% | 95.8% |
| Pig | 92% | 97.3% |
| Rabbit | 89.7% | 95.9% |
| Exon 15 | | |
| Human | 91% | 100% |
| Pig | 86.5% | 93.5% |
| Rabbit | 86.5% | 93.5% |
| Rat | 85.4% | 96.8% |

References

1. Short C E, Paddleford R R: Letter: Malignant hyperthermia in the dog. *Anesthesiology* 39:462–63, 1973.
2. Bagshaw R J, Cox R H, Knight D H, Detweiler D K: Malignant hyperthermia in a greyhound. *J. Am. Vet. Med. Assoc.* 172:61–2, 1978.
3. Bagshaw R J, Cox R H, Rosenberg H: Letter: Dantrolene treatment of malignant hyperthermia. *J. Am. Vet. Med. Assoc.* 178:1029, 1981.
4. McGrath C J, Crimi A J, Ruff J: Malignant hyperthermia in dogs. Vet. *Med/Small Animal Clin.* 77:218–20, 1982.
5. O'Brien P J, Cribb P H, White R J, Olfert E D, Steiss J E: Canine malignant hyperthermia: diagnosis of susceptibility in a breeding colony. *Can. Vet. J.* 24:172–177, 1983.
6. Cribb P H, Olfert E A, Reynolds F B. Erythrocyte osmotic fragility testing and the prediction of canine malignant hyperthermia susceptibility. *Can. Vet. J.* 27:517–522, 1986.
7. Otto K. [Malignant hyperthermia as an anesthetic complication in the dog.] *Tierarztliche Praxis* 20:519–522, 1992.
8. Nelson T E, Lin M, Zapata-Sudo G, Sudo R T: Dantrolene sodium can increase or attenuate activity of skeletal muscle ryanodine receptor calcium release channel. *Anesthesiology* 84:1368–79, 1996.
9. Fruen B R, Mickelson J R, Louis C F: Dantrolene inhibition of sarcoplasmic reticulum $Ca^{2+}$ release by direct and specific action at skeletal muscle ryanodine receptors. *J. Biol. Chem.* 272:26965–26971, 1997.
10. Klein L V. Hyperthermia in anesthetized dogs. *Modern Vet. Pract.* 56:378–380, 1975.
11. Sawyer D C: Malignant hyperthermia. *J. Am. Vet. Med. Assoc.* 179:341–44, 1981.
12. Leary S L, Anderson L C, Manning P J, Bache R J, Zweber B A: Recurrent malignant hyperthermia in a greyhound. *J. Am. Vet. Med. Assoc.* 182:521–22,1983.
13. Kirmayer A H, Klide A M, Purvance J E: Malignant hyperthermia in a dog: case report and review of the syndrome. *J. Am. Vet. Med. Assoc.* 185:978–82, 1984.
14. Bjotvedt G, Hendricks G M, Weems C W. Exertional rhabodomyolysis in a racing Greyhound/a case report. *Vet. Med./Small Animal Clin.* 78:1215–1220,1983.
15. Rand J S, O'Brien P J: Exercise-induced malignant hyperthermia in an English springer spaniel. *J. Am. Vet. Med. Assoc.* 190:1013–14, 1987.
16. O'Brien P J, Pook H A, Klip A, Britt B A, Kalow B I, McLaughlin R N, Scott E, Elliott M E: Canine stress syndrome/malignant hyperthermia susceptibility: calcium-homeostasis defect in muscle and lymphocytes. *Res. Vet. Sci.* 48:124–128,1990.
17. Dickinson P J, Sullivan M: Exercise induced hyperthermia in a racing greyhound. *Vet. Record* 135:508,1994.
18. Duncan K L, Hare W R, Buck W B. Malignant hyperthermia-like reaction secondary to ingestion of hops in five dogs. *J. Am. Vet. Med. Assoc.* 210:51–54,1997.
19. Nelson T E: Malignant hyperthermia in dogs. *J. Am. Vet. Med. Assoc.* 198:989–94, 1991.
20. McCarthy T V, Quane K A, Lynch P J: Ryanodine receptor mutations in malignant hyperthermia and central core disease. *Hum. Mutation* 15:410–17, 2000.
21. Brunson D B, Hogan K, Powers P A, Gregg R, Nelson T E: Investigation of the causal mutation for malignant hyperthermia in black Labrador Retrievers. *Canine Practice* 23:48,1998 (abstract).
22. Larach M G: Standardization of the caffeine halothane muscle contracture test. *Anesth. Analg.* 69:511–515, 1989.
23. Priat C, Hitte C, Vignaux F, Renier C, Jiang Z, Jouquand S, Cheron A, Andre C, Galibert F: A whole genome radiation hybrid map of the dog genome. *Genomics* 54:361–378,1998.
24. Mellersh C S, Hitte C, Richman M. Vignaux F, Priat C, Jouquand S, Wemer P, Andre C, DeRose S, Patterson D F, Ostrander E A, Galibert F: An integrated linkage-radiation hybrid map of the canine genome. *Mammalian Genome* 11:120–30,2000.
25. Chapman C J: A visual interface to computer programs for linkage analysis. *Am. J. Med. Genet.* 36:155–160, 1990.
26. Lathrop G M, Lalouel J M, Julier C, Ott J: Strategies for multilocus linkage analysis in humans. *Proc. Natl. Acad. Sci. USA* 81:3443–3446, 1984.
27. Lander E S, Green P: Construction of multilocus genetic maps in humans. *Proc. Natl. Acad. Sci. USA* 84:2363–2367, 1987.
28. Hastings A B, White F C, Sanders T M, Bloor C M: Comparative physiological responses to exercise stress. *J. Appl. Physiol.* 52:1077–1083, 1982.
29. Matwichuk C L, Taylor S M, Shmon C L, Kass P H, Shelton G D. Changes in rectal temperature and hematologic, biochemical, blood gas, and acid-base values in healthy Labrador Retrievers before and after strenuous exercise. *Am. J. Vet. Res.* 60:88–92, 1999.
30. Snow D H, Billeter R, Mascarello F, Carpene E, Rowlerson A, Jenny E. No classical type IIB fibres in dog skeletal muscle. *Histochemistry* 75:53–65,1982.
31. Wayne R K, Ostrander E A: Origin, genetic diversity and genome structure of the domestic dog. *Bioessays* 21:247–57, 1999.
32. Vila C, Savolainen P, Maldonado J E, Amorin I R, Rice J E, Honeycutt R L, Crandall K A, Lundeberg J, Wayne R K. Multiple and ancient origins of the domestic dog. *Science* 276:1687–1690,1997.
33. Ostrander E A, Galibert F, Patterson D F: Canine genetics comes of age. *Trends in Genetics* 16:117–124, 2000.
34. Mickelson J R, Louis C F: Malignant hyperthermia: excitation-contraction coupling, $Ca^{2+}$ release channel, and cell $Ca^{2+}$ regulation defects. *Phys. Rev.* 76:537–92, 1996.
35. Jurkat-Rott K T, McCarthy T V, Lehmann-Horn F: Genetics and pathogenesis of malignant hyperthermia. *Muscle and Nerve* 23:4–17, 2000.
36. Phillips M S, Fujii J, Khanna K, DeLeon S, Yokobata K, DeJong P J, MacLennan D H. The structural organization of the human skeletal muscle ryanodine receptor (RYR1) gene. *Genomics* 34:24–41, 1996.
37. Fujii J, Otsu K, Zorzato F, DeLeon S, Khanna V K, Weiler J E, O'Brien P J, MacLennan D H: Identification of a mutation in porcine ryanodine receptor associated with malignant hyperthermia. *Science* 253:448–451,1991.
38. Monnier N V, Procaccio V, Stieglitz P, Lunardi J: Malignant hyperthermia susceptibility is associated with a mutation of the a1-subunit of the human dihydropyridine-sensitive L-type voltage-dependent calcium-channel receptor in skeletal muscle. *Am. J. Hum. Genet.* 60:1316–25, 1997.
39. Vladutiu G D, Hogan K, Saponara I, Tassini L, Conroy J: Carnitine palmitoyl transferase in malignant hyperthermia lymphoblasts. *Muscle and Nerve* 16:485–91,1993.
40. Vladutiu G D, Taggart R T, Smail D, Lindsley H B, Hogan K. A carnitine palmitoyl transferase II (CPT2) Arg503Cys mutation confers malignant hyperthermia and variable myopathy. *Am. J. Hum. Genet.* 20:A5, 1998 (abstract).

We claim:

1. A method of determining whether a canine is susceptible to canine maliqnant hyperthermia, comprising the step of obtaining a nucleic acid sample from a canine and examining the sample for the presence.

2. The method of claim 1 wherein the nucleic acid sample is a genomic DNA sample.

3. The method of claim 2 wherein the DNA is obtained from cheek cells.

4. The method of claim 2 wherein the DNA is obtained from muscle cells.

5. The method of claim 2 wherein the DNA is obtained from blood cells.

6. A kit for determining whether a canine is susceptible to canine malignant hyperthermia comprising:

(a) a set of primers useful for amplifying at least a portion of the canine genome, wherein the amplified portion oomprises a nucleic acid encoding SEQ ID NO:1; and (b) a restriction endonuclease capable of differential cleavage in the presence or absence of a nucleic acid encoding SEQ ID NO:1.

* * * * *

UNITED STATES PATENT AND TRADEMARK OFFICE
CERTIFICATE OF CORRECTION

| | |
|---|---|
| PATENT NO. | : 6,664,059 B2 |
| APPLICATION NO. | : 09/908410 |
| DATED | : December 16, 2004 |
| INVENTOR(S) | : Kirk J. Hogan et al. |

It is certified that error appears in the above-identified patent and that said Letters Patent is hereby corrected as shown below:

Column 4, Line 44:

"lifter" should read --litter--.

Column 10, Line 62:

"a," should be --a(1)--.

Column 23, Lines 57-60 (Claim 1):

Please replace with the following paragraphs:

--A method of determining whether a canine is susceptible to canine malignant hyperthermia, comprising:

obtaining a nucleic acid sample from a canine;

amplifying the nucleic acid using a primer pair to generate an amplified segment, wherein the primer pair consists of SEQ ID NO: 19 and SEQ ID NO: 20;

digesting the amplified segment with a restriction endonuclease to generate digestion products, wherein the restriction endonuclease is MscI; and size separating the digestion products by electrophoresis, wherein the presence of both 268 and 219 bp fragments is indicative of a canine susceptible to canine malignant hyperthermia.--

UNITED STATES PATENT AND TRADEMARK OFFICE
CERTIFICATE OF CORRECTION

PATENT NO. : 6,664,059 B2
APPLICATION NO. : 09/908410
DATED : December 16, 2004
INVENTOR(S) : Kirk J. Hogan et al.

It is certified that error appears in the above-identified patent and that said Letters Patent is hereby corrected as shown below:

Column 24, Lines 57-65 (Claim 6):

Please replace with the following paragraphs:

--A Kit for determining whether a canine is susceptible to canine malignant hyperthermia comprising:

(a) a pair of primers consisting of a polynucleotide comprising SEQ ID NO: 19 and a polynucleotide comprising SEQ ID NO: 20; and (b) a restriction endonuclease Mscl.--

Signed and Sealed this

Sixth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 6,664,059 B2
APPLICATION NO. : 09/908410
DATED : December 16, 2003
INVENTOR(S) : Kirk J. Hogan et al.

It is certified that error appears in the above-identified patent and that said Letters Patent is hereby corrected as shown below:

Column 4, Line 44:

"lifter" should read --litter--.

Column 10, Line 62:

"a," should be --a(1)--.

Column 23, Lines 57-60 (Claim 1):

Please replace with the following paragraphs:

--A method of determining whether a canine is susceptible to canine malignant hyperthermia, comprising:

obtaining a nucleic acid sample from a canine;

amplifying the nucleic acid using a primer pair to generate an amplified segment, wherein the primer pair consists of SEQ ID NO: 19 and SEQ ID NO: 20;

digesting the amplified segment with a restriction endonuclease to generate digestion products, wherein the restriction endonuclease is MscI; and size separating the digestion products by electrophoresis, wherein the presence of both 268 and 219 bp fragments is indicative of a canine susceptible to canine malignant hyperthermia.--

UNITED STATES PATENT AND TRADEMARK OFFICE
CERTIFICATE OF CORRECTION

PATENT NO. : 6,664,059 B2
APPLICATION NO. : 09/908410
DATED : December 16, 2003
INVENTOR(S) : Kirk J. Hogan et al.

It is certified that error appears in the above-identified patent and that said Letters Patent is hereby corrected as shown below:

Column 24, Lines 57-65 (Claim 6):

Please replace with the following paragraphs:

--A Kit for determining whether a canine is susceptible to canine malignant hyperthermia comprising:

(a) a pair of primers consisting of a polynucleotide comprising SEQ ID NO: 19 and a polynucleotide comprising SEQ ID NO: 20; and (b) a restriction endonuclease MscI.--

This certificate supersedes the Certificate of Correction issued May 6, 2008.

Signed and Sealed this

Third Day of June, 2008

JON W. DUDAS
*Director of the United States Patent and Trademark Office*